(12) United States Patent
Law et al.

(10) Patent No.: US 6,709,868 B2
(45) Date of Patent: Mar. 23, 2004

(54) METHOD AND APPARATUS FOR MEASURING WHITE BLOOD CELL COUNT

(75) Inventors: Wai Tak Law, Moorestown, NJ (US); Yuri Nikolyukin, Moorestown, NJ (US); Inna Nikolyukin, Moorestown, NJ (US)

(73) Assignee: Portascience Inc., Moorestown, NY (US)

( * ) Notice: Subject to any disclaimer, the term of this patent is extended or adjusted under 35 U.S.C. 154(b) by 0 days.

(21) Appl. No.: 10/147,857

(22) Filed: May 20, 2002

(65) Prior Publication Data

US 2003/0215951 A1 Nov. 20, 2003

(51) Int. Cl.$^7$ .......................... G01N 31/00; G01N 21/77
(52) U.S. Cl. .................... 436/10; 436/8; 436/18; 436/63; 436/164; 436/169; 436/175; 436/177; 436/178; 422/55; 422/56; 422/73; 422/101; 435/2
(58) Field of Search .................. 436/8, 10, 18, 436/63, 164, 169, 170, 175, 177, 178; 422/55, 56, 73, 101; 435/2

(56) References Cited

U.S. PATENT DOCUMENTS

| | | | |
|---|---|---|---|
| 4,278,763 A | | 7/1981 | Berger et al. |
| 4,299,917 A | * | 11/1981 | Berger et al. ................. 435/19 |
| 4,499,185 A | * | 2/1985 | Skjold et al. ................. 435/19 |
| 4,551,428 A | * | 11/1985 | Berger et al. ................. 435/19 |
| 4,637,979 A | | 1/1987 | Skjold et al. |
| 4,645,842 A | * | 2/1987 | Corey et al. ................. 548/541 |
| 4,657,855 A | | 4/1987 | Corey et al. |
| 4,716,236 A | | 12/1987 | Ward et al. |
| 4,738,823 A | * | 4/1988 | Engelmann ................. 422/56 |
| 4,758,508 A | * | 7/1988 | Schnabel et al. ............. 435/19 |
| 4,806,423 A | | 2/1989 | Hugl et al. |
| 4,880,548 A | | 11/1989 | Pall et al. |
| 4,936,998 A | | 6/1990 | Nishimura et al. |
| 5,258,127 A | | 11/1993 | Gsell et al. |
| 5,403,745 A | | 4/1995 | Ollington et al. |
| 5,512,450 A | * | 4/1996 | Johnson et al. ................ 435/19 |
| 5,663,044 A | * | 9/1997 | Noffsinger et al. ............ 435/4 |
| 5,700,645 A | | 12/1997 | Pahuski et al. |
| 5,728,306 A | | 3/1998 | Breillatt, Jr. et al. |
| 5,783,094 A | | 7/1998 | Kraus et al. |
| 5,795,483 A | | 8/1998 | Ung-Chhun et al. |
| 5,938,940 A | | 8/1999 | Zuk, Jr. |
| 6,046,019 A | | 4/2000 | Goumeniouk et al. |
| 6,221,264 B1 | | 4/2001 | Ishida et al. |
| 6,337,026 B1 | | 1/2002 | Lee et al. |
| 6,528,652 B1 | * | 3/2003 | Huh ........................... 548/182 |

* cited by examiner

*Primary Examiner*—Maureen M. Wallenhorst
(74) *Attorney, Agent, or Firm*—Iver P. Cooper; Anne M. Kornbau

(57) ABSTRACT

A method for quantitatively measuring white blood cell count involves capture of white blood cells from a fluid sample by a retainer, removal of the red blood cells and other interfering substances by a wash solution, and reading the result of a color reaction in which an ester which is present on the white blood cells cleaves a chromogenic substrate which produces a water insoluble dye. The apparatus for use in the present method includes a retainer for white blood cells that has a dye substrate immobilized therein and an absorption layer that wicks and takes up all excess washing solution flowing past the sample.

16 Claims, 3 Drawing Sheets

METHOD AND APPARATUS FOR MEASURING WHITE BLOOD CELL COUNT

GOVERNMENT SUPPORT

The present invention was partially supported by a grant from the National Institutes of Health, Grant No. 1R43CA92976, and the U.S. government has some rights in this invention.

BACKGROUND OF THE INVENTION

1. Field of the Invention

The present invention relates to a method and device for establishing a white blood cell count in biological fluids in the presence of interfering substances.

2. Description of the Background Art

A white blood cell (WBC) count is one of the most commonly tested parameters in clinical laboratories. A laboratory WBC usually requires 5–10 ml. of venous blood, and the patient may have to wait up to three days for the laboratory results. Generally, methods for estimating WBC in biological fluids are based on automated cell counting technologies, in which the sample is diluted, and cells of different sizes and shapes are counted in a flow cell (U.S. Pat. Nos. 2,656,508; 3,502,973; 6,159,740). Instruments based on flow technology are expensive and require professionally trained personnel for running in a clinical laboratory environment. New analyzers using nanotechnology for flow cells are much smaller than the traditional cell counting instruments, but they are still in the development stage. Also, the complicated mechanical pump and valves systems required limit the options for manufacturers to offer a low cost instrument.

There are many instances in which rapid measurements of white blood cell count is important. Rapid measurements of the white blood cell count may be useful in a physician's office, where clinicians use these measurements to assess the effects of therapeutic drugs, cytostatic medications, and certain infections. Patients who are on chemotherapy also need to check their white blood cell count frequently to ensure that they are eligible for the next treatment, which may be a problem if they live at a distance from their physician or a hospital. Schizophrenic patients taking Clozapine must monitor their white blood cell counts weekly. Patients suffering from chronic infections may have white blood cell counts in excess of 10,000 cells per microliter, and should be monitored. Being able to monitor members of a large population after a radiological accident or terrorist attack would facilitate triage and planning for the best use of medical resources.

Mastitis is an inflammation of the mammary gland in an animal's udder that costs the dairy industry close to $2 billion annually in lost revenues. When a dairy animal suffers from clinical mastitis, her udder is visibly swollen or the milk is water, thick, or ropy. Unfortunately, an apparently healthy animal can harbor sub-clinical mastitis, which accounts for up to about 70% of the mastitis in dairy herds. Researchers have made many attempts to devise a test for this "invisible" mastitis. A somatic cell count (SCC) of milk, which consists of over 90% white blood cells, has been universally adopted as the measure of a mastitis infection. To date, the California Mastitis Test (CMT) is the most common test for field use. However, the CMT is labor intensive, and the test suffers from a subjective interpretation by the individual user and an unacceptably high false negative rate. There is still no suitable field test that can estimate WBC count increases resulting from sub-clinical mastitis.

For purposes of the present invention, "dairy animal" means any animal from which milk can be obtained. Non-limiting examples of dairy animals are cows, sheep, goats, camels, and buffalo (bison). Tests for white blood cells for cows can be used for other types of dairy animals as well. Thus, when the present specification uses cows as an example, the process is not limited to cows but is applicable to all types of dairy animals.

In an agricultural setting, an accurate cow-side milk test for white blood cell count means potentially large savings for farmers, who can discard the milk from mastitis infected cows before it is pooled with, and hence contaminates, the milk from uninfected cows. Estimation of WBC using a colorimetric method is very desirable to detect sub-clinical mastitis.

Enzymes located on the walls of white blood cells have esterolytic activity. Various colorless chromogenic esters known in the art may be cleaved by this enzymatic hydrolysis, resulting in the formation of a colorless acid component and a color forming alcohol or phenol component. The color intensity can be measured quantitatively by means of a calorimeter or semi-quantitatively using a visual color chart. Berger et al., in U.S. Pat. No. 4,278,763, took advantage of this esterase property and developed dipsticks capable of detecting as little as 200 cells per microliter in human urine. A number of patents have issued following this first report (U.S. Pat. Nos. 4,637,979; 4,657,855; 4,716,236; 4,806,423), and urine dipsticks for white blood cell counts have been commercialized for many years.

Unfortunately, the efficacy of assays for analytes in a biological fluid sample can be reduced by the presence of interfering substance. For example, the colorimetric WBC dipstick technologies developed for human urine are not applicable to other biological fluids, such as whole blood and milk. The intense red background color of the red blood cells in a sample of whole blood masks the color developed during the enzymatic reaction. Likewise, the complex matrix of a milk sample contains interfering substances that dramatically inhibit the enzymatic reaction. With respect to urine samples, it would be desirable to improve the dipstick performance, including reducing test time and increasing sensitivity, by circumventing the adverse effects of interfering substances.

U.S. Pat. Nos. 5,463,745 and 6,010,866, describe a method for determining an analyte in a biological fluid sample in the presence of a substance which interferes with an assay for the analyte. However, this method must be implemented using analyte specific antibodies, which makes the separation method expensive.

A number of workers have developed filters which remove or deplete white blood cells from a sample, including those described in U.S. Pat. Nos. 6,337,026; 6,221,264; 5,938,940; 5,795,483; 5,783,094; 4,880,548; 5,258,127; 5,728,306; and 4,936,998. None of these filters was disclosed for use in conjunction with white blood cell count estimations.

Diagnostic kits and methods for counting white blood cells have also been reported. U.S. Pat. No. 6,046,019 discloses a method and device that involves multiple steps performing cell lysing, filtering, substrate addition, incubation, and reading. Semi-quantitative results were reported, but this device is difficult to use.

U.S. Pat. No. 5,700,645 teaches a method for separating and concentrating cells from milk and other biological samples. This patent addresses the need for concentrating cells so as to increase the sensitivity and to separate bacterial cells for various assay. However, there is nothing in this patent about estimating white blood cell counts in the milk.

Accordingly, there is a need to develop a method and device which uses the recognized advantages of the colorimetric detection of white blood cells while providing a means for eliminating the background color and adverse effects of interfering substances.

SUMMARY OF THE INVENTION

It is an object of the present invention to overcome the aforesaid deficiencies in the cited art.

It is another object of the present invention to provide a method for estimating white blood cell count in a biological fluid.

It is a further object of the present invention to provide a device for estimating white blood cell count in a biological fluid.

It is another object of the present invention to provide a method and device for diagnosing mastitis.

It is still another method of the present invention to provide a method for estimating white blood cell count using a color reaction.

According to the present invention, white blood cell count in a biological fluid sample containing interfering substances can be obtained by capturing target cells using a membrane, and washing away interfering substances prior to the measurement step. This method and device can be used for assaying a wide variety of biological samples, such as blood, milk, urine, saliva, and sweat. Saliva can be monitored for white blood cell levels in order to detect dental problems, including infections in the gums and related parts of the mouth. Additionally, perspiration, or sweat, contains white blood cells, and thus may be monitored for levels of white blood cells present.

The method of the present invention comprises the following steps:

a. separating white blood cells from interfering substances from a biological fluid sample using a retainer which selectivity retains white blood cells;

b. removing interfering substances, such as red blood cells, enzymes, enzyme inhibitors, proteins, and lipids, from the retaining substrate, leaving only white blood cells, by washing with a washing solution containing a buffer and optional additives in water or an aqueous solution of a polar organic liquid.

c. reading, by eye or by instrument, the result of a color reaction in which an enzyme present in the white blood cells cleaves a chromogenic substrate which produces a water insoluble dye.

The chromogenic substrate can be either immobilized on the membrane or can be used as a component of the washing solution.

In a preferred embodiment, the enzyme is esterase and the chromogenic substrate is an ester.

The device of the present invention comprises:

a. a cover which has an opening for the application of a sample and a wash solution;

b. a white blood cell retainer that optionally has a dye substrate immobilized thereon;

c. an absorption layer that wicks and takes up all excess washing solution flowing past the sample;

d. a wash solution that contains a buffer, an optional reaction accelerator, and an optional dye substrate.

Figure 1:
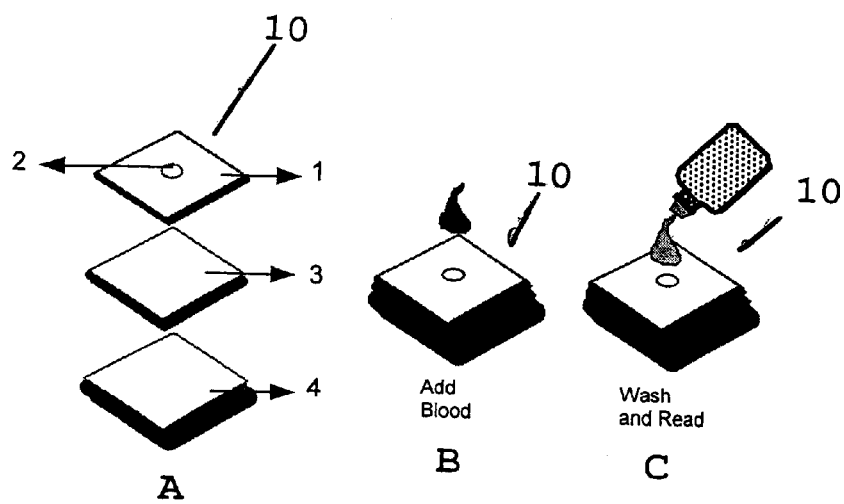
FIG. 1a shows an exploded view of the device of the present invention.
FIG. 1b shows adding a fluid sample to the device.
FIG. 1c illustrates washing the device.

| Figure legends | |
|---|---|
| 10 | device for measuring white blood cell count |
| 1 | top piece of device |
| 2 | ingress hole in top piece of device |
| 3 | white blood cell capturing membrane |
| 4 | water-absorbent layer |

DETAILED DESCRIPTION OF THE PREFERRED EMBODIMENTS OF THE INVENTION

The present invention can be used for determining white blood cell counts in biological fluids such as whole blood, urine, milk, perspiration, and saliva in the presence of interfering substances. Among the interfering substances from which the white blood cells are separated are red blood cells, enzymes, enzyme inhibitors, reducing agents, proteins, lipids, etc. This method involves using a retainer which the sample can quickly traverse, which retainer rapidly captures white blood cells and will hold onto the white blood cells after red blood cells and other interfering substances are washed away.

Examples of commercially available retainers which rapidly capture white blood cells and retain them on the membrane during washing include membranes Leukosorb A and B (Pall Inc., Long Island, N.Y.), which are designed for filtering white blood cells from blood intended for transfusions, and which can capture 30–80% of the white blood cells from whole blood by their well-controlled surface charge and pore sizes. The retainers have pore sizes (or mesh sizes) in the range of about 3 to about 15 microns, and a net positive surface charge. The combination of pore (or mesh) size plus the net positive surface charge enables the retainer to capture white blood cells on the surface thereof, while other substances, such as red blood cells, lipids, proteins, etc., pass through the retainer. When the white blood cells are retained on the retainer, the net positive surface charge of the retainer keeps the white blood cells, which have a negative surface charge, from being washed off by the washing solution. It was surprisingly found that, when a sample of whole blood comprising about 5 to about 13 microliters of whole blood was applied to these retainers, substantially 100% of the white blood cells were almost instantaneously captured by the retainers. Therefore, these membranes were found to be useful in developing a quantitative white blood cell measuring device. Other retainer materials that possess positively charged surfaces, such as certain grades of cellulose paper, have been found to exhibit the same behavior with respect to white blood cells, and these materials can successfully be used as retainers in the method of the present invention.

There are enzymes on the surface of white blood cells that can be used to detect the presence and amount of white blood cells in a fluid by catalyzing a chromogenic substrate to produce a visible dye. There are many commercial tests available for detecting esterase, which are well known to those skilled in the art. The preferred substrate is a member of the indoxyl ester family, such as 3-acetyl indoxyl and 3-(N-tosyl-L-alanyloxy)-indole. However, any known substrate that can be hydrolyzed by the esterase on white blood cells to form a colored dye can be used. Examples of such dyes are given in Corey et al., U.S. Pat. No. 4,657,855, the entire contents of which are hereby incorporated by reference. One skilled in the art can readily determine what dyes are suitable for this purpose. The substrate can be immobilized onto the retainer as a dried reagent, or it can be incorporated into the wash solution.

The wash solution removes all substances not captured by the retainer, i.e., substances that will interfere with rapid detection of white blood cells based on their enzymatic activity. The wash solution is based either on water or on a mixture of water and a polar organic solvent along with a buffer, and other optional ingredients. Nonlimiting examples of polar organic solvents include methanol, ethanol, acetone, and the like.

For point-of-care application, it is desirable to speed up the reaction time to less than five minutes per assay. Accelerators such as certain heterocyclic compounds and alcohols have been shown to be helpful in speeding up the assay time for white blood cells, as described in U.S. Pat. No. 4,299,917, the entire contents of which are hereby incorporated by reference. It was also surprisingly found that a buffer which maintained the pH at from about 8 to about 11 was even more effective than an accelerator in reducing the time for assay. More specifically, about 5 mM to about 200 mM TRIS buffer at pH about 9.5 to about 10.5 was found to be most effective in providing the fastest reaction rate without increasing the background color significantly. The wash solution must be chosen such that most interfering substances can be flushed from the capture membrane into the absorption pad instantaneously.

The absorption pad can be made of any conventional absorptive material. Inexpensive cellulose materials are suitable for this, such as Schliecher & Schuell 900 filter paper. This paper has the porosity and capacity to wick up to 300 microliters of washing solution from the capture membrane instantaneously.

FIG. 1 illustrates the device of the present invention. The device 10 consists of three major pieces. The top piece, 1, is a plastic material about 5–10 micrometers thick with pressure sensitive adhesive at the bottom and a hole 2 of about 3–10 mm punched in the middle. Below that is a white blood cell capture membrane 3 that has optional dye-ester substrate immobilized throughout its structure. The third layer 4 is a thick water absorbent layer made of cellulose fibers.

As shown in FIG. 1b, a biological fluid sample containing white blood cells is first introduced into the opening 1 on top of the device. The white blood cell capturing membrane 3 is very hydrophilic and quickly absorbs the sample. The membrane instantaneously captures the white blood cells in the sample. As shown in FIG. 1c, about three to four drops of wash solution are then introduced through the opening, washing most or all of the red blood cells and/or other interfering substances into the absorption layer 4. The white blood cells captured in the first layer catalyze the hydrolysis of the dye-substrate, resulting in color formation.

Figure 2:
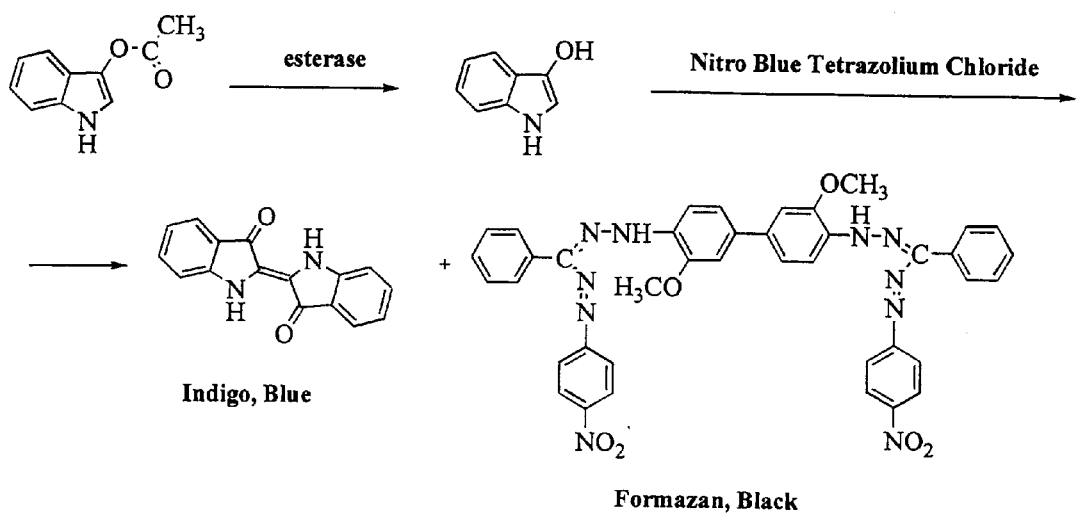
FIG. 2 illustrates a reaction mechanism for a dye.
Figure 3:
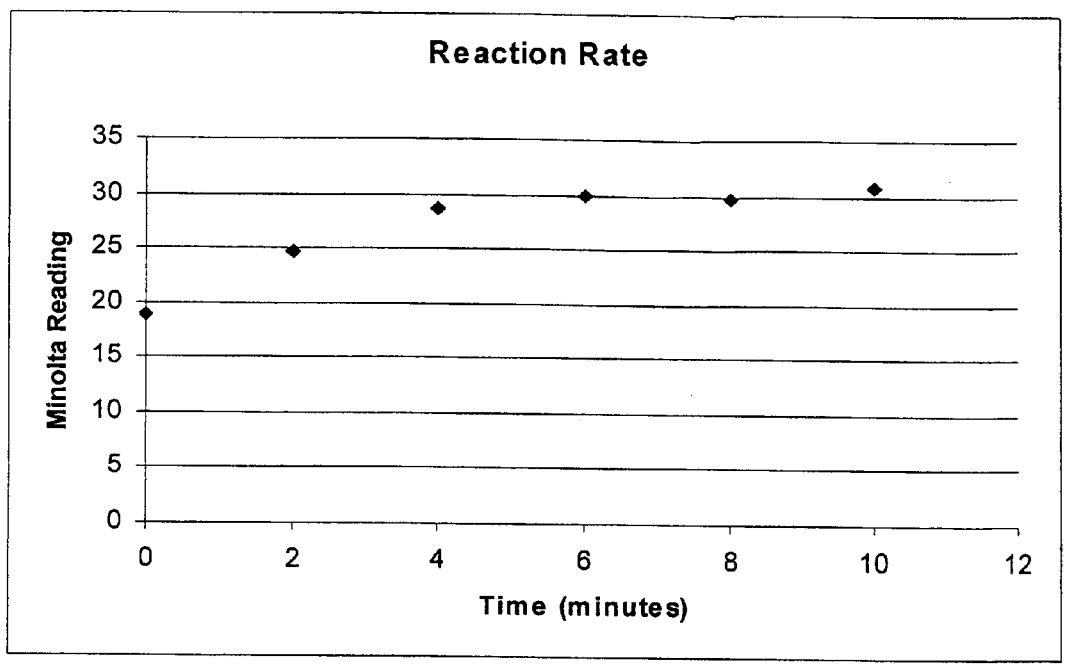
FIG. 3 illustrates the rate of the reaction of the esterase with the substrate.

The actual reaction mechanism using 3-acetyl indoxyl and nitro blue tetrazolium chloride as a dye substrate is shown in FIG. 2. The colored dyes formed are water insoluble, so that the color developed on the top of the membrane will not be washed away. The color was found to be directly proportional to the number of white blood cells captured into the first layer. Since any red blood cells and/or other interfering substances were already washed away by the wash solution the resulting dark blue green color can be read semi-quantitatively by visually comparing it to a color scale. For a quantitative reading, a reflectometer is used. FIG. 3 represents the rate of the reaction in which the color formation is plotted versus time.

The following nonlimiting examples further illustrate the present invention.

EXAMPLE 1

Whole Blood WBC Test

Figure 4:
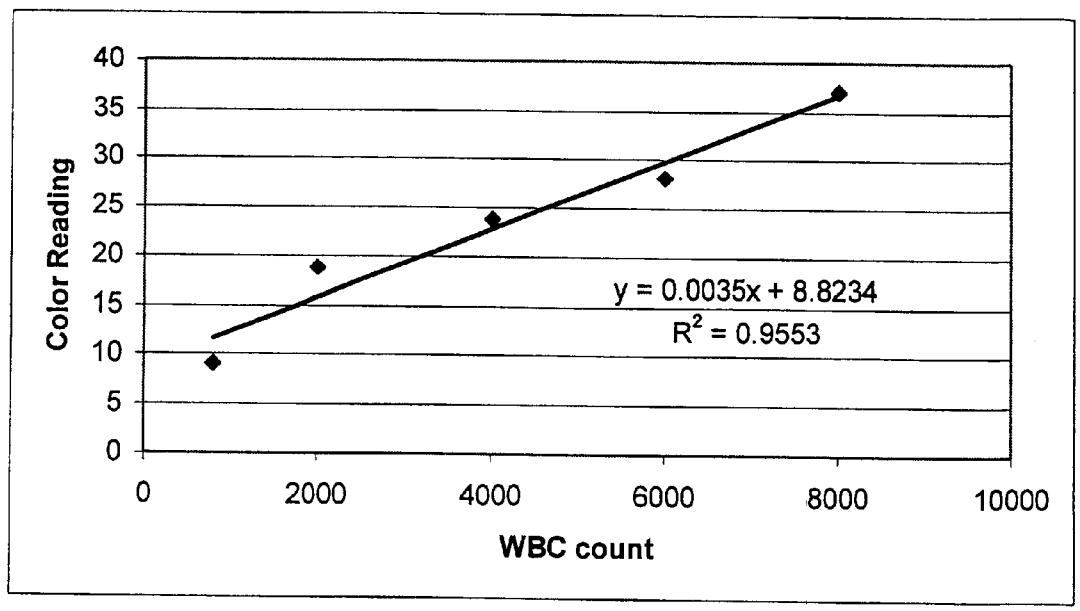
FIG. 4 correlates the white blood cell count with color readings.

Five milligrams of 3-acetyl-indoxyl substrate was dissolved in absolute ethanol and the substrate was used to impregnate a WBC capture membrane (Leukosorb B, Pall, Inc, NY). The membrane was then dried in an oven at 40° C. for 15 minutes. A wash solution was prepared by dissolving 5 mg of NBT (Nitro Blue Tetrazolium Chloride monohydrate) per mL of saline solution. The devices were assembled as shown in FIG. 1a. A citrated whole blood sample with a count of 8000 white blood cells per microliter was diluted serially with saline to give counts of 8, 6, 4, 2, and 0.8 thousand WBC per microliter. Thirty microliters of each sample was pipetted onto the top of the device. After each addition of sample, 250 microliters of wash solution was pipetted onto the device to wash out the red blood cells and begin the enzymatic reaction. The color intensity developed after 10 minutes was measured with a Minolta CR321 chromameter through the top opening of the device. A plot of the color measurements versus the instrumentally obtained white blood cell count in a range of 800 to 8000 counts per microliter is shown in FIG. 4. This formulation showed a detection limit of at least 800 cells per microliter.

EXAMPLE 2

WBC Count Test for Milk

Milk contains substances that inhibit esterase activity, which means that the sensitivity of esterase tests for white blood cells counts varies, depending upon the amount of these interfering substances. The esterase activity in milk can range from about 10% to about 90% of the amount of esterase actually present in the milk, depending upon the amount of proteins, enzymes inhibitors, etc. present in the milk. Therefore, it is essential to remove these interfering substances prior to conducting a white blood cell count in milk. Table 1 shows an example of decreased esterase activity in milk.

Test devices were constructed by first dissolving 10 mg/mL of 3-(N-tosyl-L-alanyloxy)-indole in 100% ethanol. This solution was used to impregnate Whatman filter paper. The wash solution was 100 mM Tris (pH=10) buffer. Forty microliters of milk sample was introduced into the sample well of the test device, immediately followed by 160 microliters of wash solution. The test devices were read with a Minolta CR 321 chromameter after ten minutes.

Figure 5:
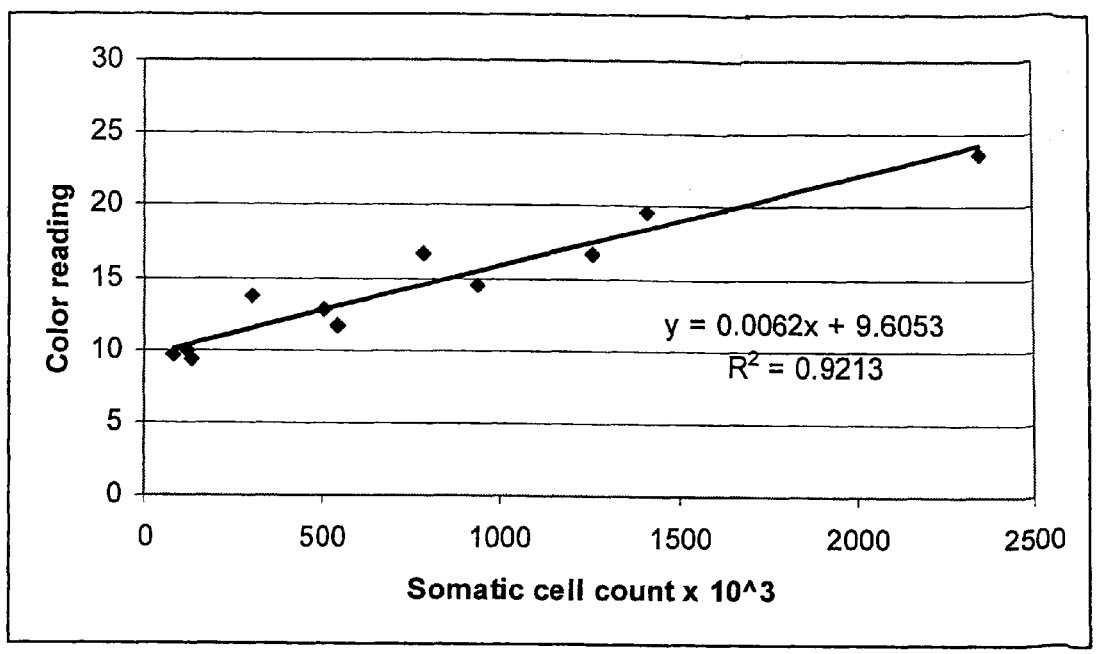
FIG. 5 correlates the somatic cell count with color readings.

Eleven fresh milk samples were obtained from a local dairy farm. These samples were split. Somatic cell counts were measured in a reference laboratory by flow cytometer, and the white blood cell counts were estimated by test devices. The test devices showed a lower detection limit of 100 cells per microliter. The correlation of color development versus somatic cell counts is shown in FIG. 5. The test devices showed a good correlation with the reference cell count method using a flow cytometer, with a correlation coefficient of 0.965.

TABLE 1

Inhibition Effect of Interfering Substances in Milk on Esterase

|  | Buffer | Milk |
|---|---|---|
| Color intensity of dipstick read After 10 minutes by a chromameter | 40.4 | 17.2 |

EXAMPLE 3
WBC Test for Human Urine

Test devices were constructed according to Example 2. Four urine samples from patients with urinary tract infections were assayed using the test devices as well as by a dip stick method using the same reagent pad. Table 2 shows that the test device was much more sensitive to the white blood cells in urine than the dipstick version using the same formulation.

TABLE 2

Color Readings by a Minolta Chromameter

| Urine (Cells per microliter) | 200 | 600 | 1500 | 2000 |
|---|---|---|---|---|
| Test Device Reading | 4.0 | 10.7 | 26.8 | 37.8 |
| Dip Stick Reading | 6.3 | 7.1 | 8.0 | 10.2 |

The present invention thus provides a method and device for counting white blood cells in physiologic fluids such as blood, urine, or milk. The device can be used in a variety of medical, home care agricultural, and disaster situations. The device can be used, for example, for quick measurements of the white blood cell count in a physician's, office, or for patients to use at home to monitor white blood cell count. The method and device are also useful in a dairy to monitor the dairy animals for mastitis.

The process and device of the present invention can be used to monitor CD4, which is a component of white blood cells. This is particularly important in treating AIDS patients with a cocktail drug therapy, as there are more than 60 different cocktails presently available for treating AIDS, and it is important to monitor the effectiveness of the drugs by monitoring CD4 as well as viral load. Heretofore, a flow cytometer was required to monitor CD4, which equipment is generally only available in a well-equipped hospital or commercial laboratory.

To monitor CD4, a labeled antibody to CD4 is incubated with a sample. The sample is then applied to the device of the present invention, and any CD4-antibody conjugates are retained on the retainer. The retainer is washed to remove interfering substances, and the label on the antibody is read. If very little or no CD4 is present in the sample, all of the labeled antibody will be washed out with the other interfering substances. However, whatever CD4 is present in the sample will be retained on the retainer, and the label can be read to indicate the CD4.

All references cited herein, including prior applications and patents, are hereby incorporated by reference in their entirety.

The foregoing description of the specific embodiments will so fully reveal the general nature of the invention that others can, by applying current knowledge, readily modify and/or adapt for various applications such specific embodiments without departing from the generic concept, and, therefore, such adaptions and modifications should and are intended to be comprehended within the meaning and range of equivalents of the disclosed embodiments. It is to be understood that the phraseology or terminology employed herein is for the purpose of description and not of limitation.

What is claimed is:

1. A method for counting white blood cells in a sample comprising:

a. capturing white blood cells from the sample on a retainer that has a net positive charge;

b. removing interfering substances from the white blood cells captured on the retainer by washing the retainer with a washing solution;

c. contacting the white blood cells with a chromogenic substrate cleaved by an enzyme present on the white blood cells which produces a water insoluble dye, wherein said substrate is either immobilized on a membrane or comprises part of the washing solution; and d. reading a color change resulting from the enzyme present in the white blood cells.

2. The method according to claim 1 wherein the enzyme is esterase.

3. The method according to claim 1 wherein the sample is selected from the group consisting of blood, milk, urine, saliva, and perspiration.

4. The method according to claim 1 wherein the wash solution contains a buffer, an optional reaction accelerator, and an optional second substrate for the enzyme.

5. The method according to claim 4 wherein the buffer has a pH range of from about 8 to about 11.

6. The method according to claim 5 wherein the buffer has a pH range of from about 9 to about 10.5.

7. The method according to claim 4 wherein the wash solution contains both water and a polar organic solvent.

8. The method according to claim 4 wherein the wash solution contains a nonionic surfactant.

9. The method according to claim 1 wherein the white blood cells contain a CD4 component.

10. A method for detecting mastitis comprising counting white blood cells in a sample of milk comprising:

a. capturing white blood cells from the sample on a retainer which has a net positive charge;

b. removing interfering substances from the white blood cells captured on the retainer by washing the retainer with a washing solution;

c. contacting the white blood cells with a chromogenic substrate cleaved by an enzyme present on the white blood cells which produces a water insoluble dye, wherein said substrate is either immobilized on a membrane or comprises part of the washing solution; and d. reading a color change resulting from the enzyme present in the white blood cells.

11. The method according to claim 10 wherein the enzyme is esterase.

12. A device for counting white blood cells comprising:

a. a white blood cell capture retainer on which is immobilized a dye substrate and b. an absorption layer below the capture retainer that wicks and takes up excess washing solution flowing past a sample of white blood cells on the retainer.

13. The device according to claim 12 wherein the retainer has a pore size ranging from about 3 to about 15 microns and a net positive charge.

14. The device according to claim 13 wherein the retainer is a porous membrane.

15. The device according to claim 12 further including a plastic cover which is placed on top of the retainer having an opening for application of sample and wash solution.

16. A method for detecting CD4 in a sample comprising:

a. Adding a labeled antibody to CD4 to a sample;

b. Applying the sample plus antibody to a device according to claim 12 whereby any CD4-antibody conjugates are retained on the retainer in the device;

c. Washing the retainer to remove interfering substances; and d. reading the label on the antibody to determine how much CD4 was present in the sample.

* * * * *